United States Patent [19]

Haag et al.

[11] 4,117,026
[45] Sep. 26, 1978

[54] SELECTIVE PRODUCTION OF PARA DIALKYL SUBSTITUTED BENZENES

[75] Inventors: Werner O. Haag, Lawrenceville; David H. Olson, Pennington, both of N.J.

[73] Assignee: Mobil Oil Corporation, New York, N.Y.

[21] Appl. No.: 841,073

[22] Filed: Oct. 11, 1977

Related U.S. Application Data

[63] Continuation-in-part of Ser. No. 685,869, May 12, 1976, abandoned, and Ser. No. 685,872, May 12, 1976, abandoned.

[51] Int. Cl.$^2$ ............................ C07C 3/52; C07C 3/62
[52] U.S. Cl. ............................ 260/671 R; 260/671 C; 260/672 T; 260/673; 260/673.5
[58] Field of Search ........... 260/671 R, 671 C, 672 T, 260/673, 673.5; 252/455.2; 423/328

[56] References Cited

U.S. PATENT DOCUMENTS

| 3,751,504 | 8/1973 | Keown et al. | 260/671 C |
|---|---|---|---|
| 3,926,782 | 12/1975 | Plank et al. | 208/135 |
| 3,957,621 | 5/1976 | Bonacci et al. | 208/60 |

Primary Examiner—C. Davis
Attorney, Agent, or Firm—Charles A. Huggett; Raymond W. Barclay

[57] ABSTRACT

A catalytic process is provided for the selective production of para dialkyl substituted benzenes containing alkyl groups of 1 to 4 carbon atoms, typified by paraxylene, by contacting, under conversion conditions, a hydrocarbon precursor selected from the group consisting of mono alkyl-substituted benzenes having 1-4 carbon atoms in the alkyl substituent, e.g., toluene, ethyl benzene, propyl benzene, or butyl benzene; a $C_2$-$C_{15}$ olefin and a $C_3$-$C_{60}$ paraffin, or mixtures thereof including mixtures of benzene with at least one of the aforementioned olefins or paraffins with a zeolite-containing catalyst characterized by a xylene sorption capacity greater than 1 gram/100 grams of zeolite and an ortho xylene sorption time for 30 percent of said capacity of greater than 10 minutes, said sorption capacity and sorption time being measured at 120° C and a xylene pressure of 4.5 ±0.8 mm. of mercury, said catalyst comprising a crystalline aluminosilicate zeolite having a silica to alumina ratio of at least about 12 and a constraint index, as hereinafter defined, within the approximate range of 1 to 12 and recovering from the resulting product mixture, a para dialkyl substituted benzene in an amount greater than the thermodynamic equilibrium concentration thereof in total dialkyl substituted benzenes produced.

25 Claims, 3 Drawing Figures

SELECTIVE PRODUCTION OF PARA DIALKYL SUBSTITUTED BENZENES

CROSS REFERENCE TO RELATED APPLICATIONS

This application is a continuation-in-part of copending applications Ser. Nos. 685,869 and 685,872, both filed May 12, 1976 and both now abandoned.

BACKGROUND OF THE INVENTION

1. Field of the Invention

This invention relates to a process for converting certain precursors to a high yield of para dialkyl substituted benzenes, such as para-xylene, utilizing a specified crystalline aluminosilicate zeolite catalyst.

2. Description of the Prior Art

The disproportionation of aromatic hydrocarbons in the presence of zeolite catalysts has been described by Grandio et al. in the *Oil and Gas Journal*, Vol. 69, No. 48 (1971). U.S. Pat. Nos. 3,126,422; 3,413,374; 3,598,878; 3,598,879 and 3,607,961 show vapor-phase disproportionation of toluene over various catalysts.

In these prior art processes, the xylene product produced has the equilibrium composition of approximately 24 percent para, 54 percent meta and 22 percent ortho.

While the above-noted prior art is considered of interest in connection with the subject matter of the present invention, the conversion process described herein, utilizing a catalyst of particularly defined sorption properties comprising a crystalline aluminosilicate zeolite characterized by a silica to alumina ratio of at least about 12 and a constraint index within the approximate range of 1 to 12, has not, insofar as is known, been heretofore described.

Of the xylene isomers, i.e., ortho, meta and para-xylene, meta-xylene is the least desired product, with ortho and para-xylene being the more desired products. Para-xylene is of particular value being useful in the manufacture of terephthalic acid which is an intermediate in the manufacture of synthetic fibers, such as "Dacron". Mixtures of xylene isomers, either alone or in further admixture with ethylbenzene, generally containing a concentration of about 24 weight percent para-xylene in the equilibrium mixture, have previously been separated by expensive superfractionation and multistage refrigeration steps. Such process, as will be realized, has involved high operation costs and has a limited yield.

SUMMARY OF THE INVENTION

In accordance with the present invention, there has been discovered a process for the selective production of para dialkyl substituted benzenes wherein the alkyl group contains from 1 to 4 carbon atoms, such as para-xylene, by contacting, under conversion conditions, a hydrocarbon precursor selected from the group consisting of mono alkyl substituted benzenes having 1-4 carbon atoms in the alkyl substituent; a $C_2$-$C_{15}$ olefin and a $C_3$-$C_{60}$ paraffin or mixtures thereof including mixtures of benzene with at least one of the aforementioned olefins or paraffins, with a catalyst comprising a crystalline aluminosilicate zeolite essentially characterized by a silica to alumina ratio of at least about 12 and a constraint index within the approximate range of 1 to 12. The catalyst is further characterized by a xylene sorption capacity greater than 1 gram/100 grams of zeolite and an ortho xylene sorption time for 30 percent of said capacity of greater than 10 minutes, the sorption capacity and sorption time being measured at 120° C. and a xylene pressure of 4.5 ± 0.8 mm. of mercury.

In a preferred embodiment, the present process comprises conversion of the specified precursors to yield xylenes in which the proportion of para-xylene is substantially in excess of its normal equilibrium concentration and preferably in excess of 40 weight percent of the xylene product produced in the presence of the specified catalyst at a temperature between about 250° and about 750° C. at a pressure between about 0.1 and about 100 atmospheres utilizing a feed weight hourly space velocity (WHSV) between about 0.1 and about 2000. The latter WHSV is based upon the weight of catalyst compositions, i.e., total weight of active catalyst and binder therefor. The effluent is separated and distilled to remove the desired product, e.g., para-xylene and unreacted product is recycled for further reaction.

DESCRIPTION OF SPECIFIC EMBODIMENTS

Figure 1:
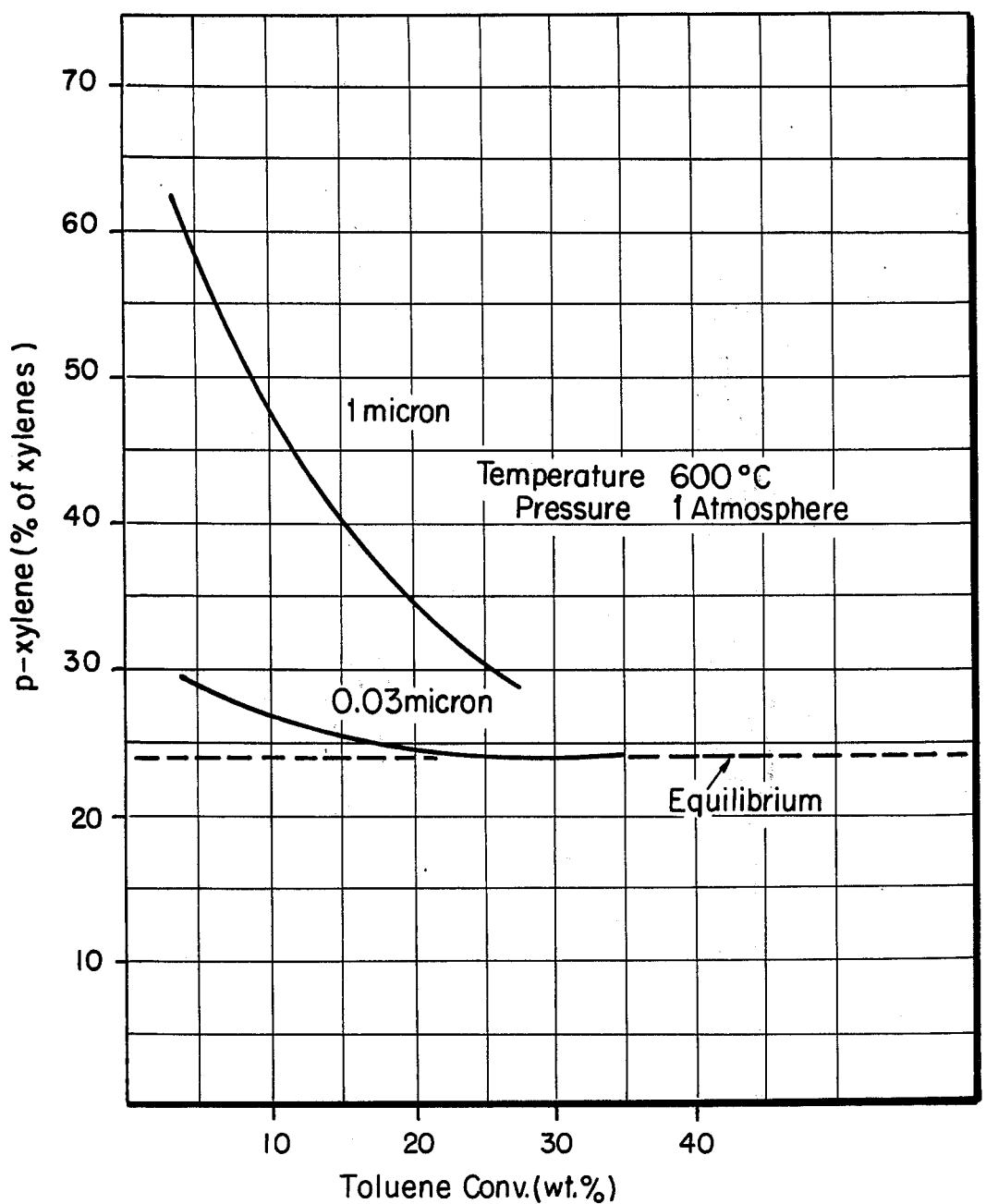
FIG. 1 shows a comparison of the para-xylene selectivity achieved with small and large crystal crystalline aluminosilicate zeolite catalyst.

The hydrocarbon precursor charge utilized in the process of this invention may be toluene, a $C_2$-$C_{15}$ olefin such as ethylene, propylene, butenes, pentenes, hexenes, heptenes, octenes, nonenes, decenes, pentadecenes, or mixtures thereof with one another or a $C_3$-$C_{60}$ paraffin such as butane, hexane, octane, dodecane, eicosane, dotriacontane, tetracontane, or mixtures thereof with one another. Preferably, such paraffins are straight chain or only slightly branched.

Typical of the processes contemplated herein are disproportionation of toluene to benzene and xylene, wherein the proportion of para-xylene obtained is greatly in excess of its normal equilibrium concentration. Such process is effectively carried out at a temperature of between about 400° C. and about 700° C. at a pressure between about 1 atmosphere and about 100 atmospheres utilizing a weight hourly space velocity of between about 1 and about 50.

Another charge stock suitable for use in the process of the invention is a stream high in $C_2$-$C_{15}$ olefin content. Thus, ethylene, propylene, butenes, pentenes, hexenes, dienes such as butadiene, pentadienes, cycloolefins such as cyclopentane and cyclohexene, alkyl-substituted cycloolefins such as ethyl cyclopentene, cyclopentadiene and cyclohexadiene can be effectively converted to a high yield of para dialkyl substituted benzenes utilizing the hereinabove described catalyst. Conversion utilizing such olefin feed is carried out at a temperature within the approximate range of 300° to 700° C., a pressure between atmospheric and 100 atmospheres employing a weight hourly space velocity between about 1 and about 1000. As sources of the olefin reactant either substantially pure streams of the $C_2$-$C_{15}$ olefin may be employed or refinery or chemical streams high in such reactant, i.e., generally more than 25 volume percent may be used.

A still further charge stock which can be effectively used in the present invention to selectively produce para dialkyl substituted benzenes containing alkyl groups of 1 to 4 carbon atoms includes paraffinic hydrocarbons having between 3 and 60 carbon atoms. Representative of such paraffins are butanes, pentanes, hexanes, heptanes, octanes, dodecanes, eiconsane, dotriacontane, tetracontane and alkyl-substituted derivatives of these paraffins. Utilizing such paraffinic charge, reaction conditions include contact with the crystalline aluminosilicate zeolite catalyst at a temperature of between about 300° t 700° C., a pressure between about atmospheric and about 100 atmospheres and a weight hourly space velocity between about 0.1 and about 100.

The use of mixed aromatics as feed is also feasible. For example, a mixture of ethylbenzene and toluene is converted selectively to a mixture rich in p-diethylbenzene and p-ethyltoluene, the latter predominating at high toluene to ethylbenzene ratios in the feed.

Reaction of benzene, toluene, ethylbenzene, propylbenzene or butylbenzene with $C_2$-$C_{20}$ olefins or $C_5$-$C_{25}$ paraffins at 250° to 500° C. yields p-dialkyl benzenes. This reaction is preferably carried out under pressure greater than 200 psig.

For example, benzene and ethylene at a mole ratio of 1:2 to 10:1 yield p-diethylbenzene besides ethylbenzene. ($p$ = 400 psig, Temp. = 800° F.); toluene and 1-octene yield p-ethyltoluene and a mixture of n- and isopropyl toluene rich in p-isomer.

In the absence of added aromatics, $C_2$-$C_{15}$ olefins and $C_3$-$C_{60}$ paraffins each yield a mixture or aromatics rich in p-dialkylbenzenes. The olefins and the higher paraffins are more reactive and require lower severity of operation, e.g., a temperature of 250°-600° C., and preferably 300°-550° C., while the lower paraffins, e.g., $C_3$-$C_5$ paraffins yield aromatics at a practical rate only above 400° C. The aromatization can be carried out at atmospheric pressure or at elevated pressure; low pressure hydrogen can be used to retard catalyst aging, but high hydrogen partial pressure above 200 psig diminishes aromatics' formation. Production of p-dialkylated benzenes containing alkyl groups greater than $C_1$ is favored by higher pressure and lower temperature; for example, p-ethyltoluene is formed from either dodecene or 1-butene at 400° C., whereas p-xylene is the preferred dialkylbenzene formed at higher temperature.

In accordance with the present invention the above described feed precursors are brought into contact, under conversion conditions, with a bed comprising particle-form catalyst containing a crystalline aluminosilicate zeolite, which catalyst is characterized by: (1) an activity, in terms of alpha value, of between about 2 and about 5000, (2) a xylene sorption capacity greater than 1 gram/100 grams of zeolite and (3) an ortho-xylene sorption time for 30 percent of said capacity of greater than 10 minutes, where the sorption capacity and sorption time are measured at 120° C. and a xylene pressure of 4.5 ± 0.8 mm. of mercury.

The alpha value reflects the relative activity of the catalyst with respect to a high activity silica-alumina cracking catalyst. To determine the alpha value as such term is used herein, n-hexane conversion is determined at about 1000° F. Conversion is varied by variation in space velocity such that a conversion level of 10 to 60 percent of n-hexane is obtained and converted to a rate constant per volume of zeolite and compared with that of silica-alumina catalyst which is normalized to a reference activity of 1000° F. Catalytic activity of the catalysts are expressed as multiple of this standard, i.e., the silica-alumina standard. The silica-alumina reference catalyst contains about 10 weight percent $Al_2O_3$ and remainder $SiO_2$. This method of determining alpha, modified as described above, is more fully described in the Journal of Catalysis, Vol. VI, Pages 278–287, 1966.

The aforenoted xylene sorption characteristics reflect diffusion properties of the crystalline aluminosilicate zeolite-containing catalyst employed. Such zeolite, as hereinafter described in greater detail, has a silica to alumina ratio of at least about 12 and a constraint index within the approximate range of 1 to 12. This zeolite, in unmodified form, as crystallized with a minimum crystal dimension of less than about 0.5 micron, has an ortho-xylene sorption time for 30 percent of xylene sorption capacity, measured under the above-noted conditions, of considerably less than 10 minutes and hence is unsuitable for use as a catalyst in the present process directed to selective production of para dialkyl substituted benzenes wherein the alkyl group contains from 1 to 4 carbon atoms.

It is only by modification of the diffusivity of the above-noted type zeolite that a catalyst is obtained which is capable of achieving selective formation of the desired para dialkyl-substituted benzene. Thus, considering selective production of para-xylene, such is obtained if ortho and meta xylene, produced within the zeolite crystal, can isomerize to para-xylene at a rate which is greater than their diffusion out of the zeolite pores.

Requisite diffusivity characteristics for the crystal aluminosilicate zeolite-containing catalyst used in the present process are obtained by modification of the crystalline aluminosilicate zeolite employed prior to use by combining therewith a small amount, generally in the range of about 2 to about 30 weight percent, of a difficulty reducible oxide, such as oxides of antimony, boron, phosphorus, magnesium or combinations thereof. Prior modification of the zeolite may also be suitably effected by precoking to deposit at least about 1 weight percent of coke thereon. Another means of achieving desired diffusivity is with use of large crystal size zeolite having a minimum crystal dimension of greater than about 0.5 micron, generally in the approximate range of 1–20 microns and particularly 1–6 microns. In a preferred embodiment, the specified large crystal size zeolite modified by precoking or combination therewith of one or more of the aforementioned difficultly reducible oxides is employed.

In assessment of zeolite crystal size, conventional scanning electron microscopy (SEM) techniques can be used, the minimum crystal dimension of a given crystal being taken as the dimension of reference. The crystalline aluminosilicate zeolites used in the present invention in substantial proportion are essentially characterized by a minimum crystal dimension of greater than about 0.5 micron. It is contemplated that the amount of zeolite of such crystal size will be such as to exert a directive influence in the desired selective production of paradialkyl substituted benzenes. Generally, the amount of zeolite of such crystal size will be present in predominate proportion, i.e, in an amount exceeding 50 weight percent, and preferably may constitute up to 100 weight percent of the total zeolite employed.

In addition to the use of scanning electron microscopy as a tool in the selection of an effective crystalline aluminosilicate zeolite for use in the catalyst employed herein, the measurement of hydrocarbon sorption capacities and rates have been useful in characterizing the catalyst. Such measurements are conveniently carried out gravimetrically in a thermal balance. In particular, it has been found that an equilibrium sorption capacity of xylene, which can be either para, meta, ortho or a mixture thereof, preferably para-xylene since this isomer reaches equilibrium within the shortest time, of at least 1 gram per 100 grams of zeolite measured at 120° C. and a xylene pressure of 4.5 ± 0.8 mm. of mercury and an orthoxylene sorption time for 30 percent of said capacity of greater than 10 minutes (at the same conditions of temperature and pressure) are required in order to achieve the desired selective production of para dialkyl substituted benzenes.

It has been found that zeolites exhibiting very high selectivity for para-dialkylbenzene production require a very long time up to and exceeding a thousand minutes to sorb o-xylene in an amount of 30% of total xylene sorption capacity. For those materials it is more convenient to determine the sorption time for a lower extent of sorption, such as 5%, 10% or 20% of capacity, and to estimate the 30% sorption time by applying the following multiplication factors F as illustrated for 5% sorption:

| $t_{0.3} = F \cdot t_{0.05}$ | |
|---|---|
| Percent of sorption capacity | Factor(F) to Estimate 30% Sorption Time |
| 5 | 36 |
| 10 | 9 |
| 20 | 2.2 |

The zeolites herein described are members of a novel class exhibiting some unusual properties. These zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e., high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperature which induces irreversible collapse of the framework of other zeolites, i.e., of the X and A type. Furthermore, carbonaceous deposits, when formed, may be removed by burning at higher than usual temperatures to restore activity. In many evironments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} (\text{fraction of n-hexane remaining})}{\log_{10} (\text{fraction of 3-methylpentane remaining})}$$

The constraint index approximates the ratio of the cracking rate constants for the two hydrocarbons. Zeolites suitable for the present invention are those having a constraint index in the approximate range of 1 to 12.

Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 500° F. to 950° F., with accompanying conversion between 10% and 60%, the constraint index may vary within the indicated approximate range of 1 to 12. Likewise, other variables such as the crystal size of the zeolite, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° F., to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated by reference.

ZSM-38 is more particularly described in U.S. Pat. No. 4,046,859, the entire contents of which are incorporated herein by reference.

The specific zeolites described, when prepared in the presence of organic cations, are catalytically inactive, possible because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5 particularly preferred.

In a preferred aspect of this invention, the zeolites hereof are selected as those having a crystal framework density, in the dry hydrogen form, of not substantially below about 1.6 grams per cubic centimeter. It has been foudn that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII to the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

In a preferred embodiment, the crystalline aluminosilicate zeolites employed, particularly those having a minimum crystal dimension of greater than about 0.5 micron, may have undergone modification prior to use by selective precoking thereof to deposit at least about 1 weight percent and generally between about 2 and about 40 weight percent of coke thereon, based on the weight of total catalyst. If zeolite is employed in substantially pure form or in combination with a low coking binder, such as silica, then the weight percent of coke is generally in the range of 2 to 10 weight percent. When the zeolite is combined with a binder of high coking tendencies, such as alumina, coke content of the total catalyst is in the approximate range of 10 to 40 weight percent. Precoking can be accomplished by contacting the catalyst with a hydrocarbon charge, e.g., toluene, under high severity conditions or alternatingly at a reduced hydrogen to hydrocarbon concentration, i.e., 0 to 1 mole ratio of hydrogen to hydrocarbon for a sufficient time to deposit the desired amount of coke thereon. Prior modification of the zeolite may also be suitably effected by combining therewith a small amount, generally in the range of about 2 to about 30 weight percent, of a difficulty reducible oxide, such as oxides of antimony, phosphorus, boron or magnesium. Combination of the desired oxide with the zeolite can readily be effected by contacting the zeolite with a solution of an appropriate compound of the element to be introduced, followed by drying and calcining to convert the compound to its oxide form.

The conversion process described herein may be carried out as a batch type, semi-continuous or continuous operation utilizing a fixed or moving bed catalyst system. The catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the charge stock. It is particularly feasible to conduct the desired conversion in the presence of hydrogen utilizing a hydrogen/precursor mole ratio of between about 2 and about 20, with hydrogen pressure extending from 1 atmosphere up to 100 atmospheres. The presence of hydrogen in the reaction zone has been found to very substantially reduce the aging rate of the catalyst.

While the above process has been described with reference to selective production of para dimethyl substituted benzenes typified by para-xylene, it is contemplated that other para dialkyl substituted benzenes, wherein the alkyl group contains from 1 to 4 carbon atoms may similarly be selectively produced. Thus, utilizing the technique described herein, it is contemplated that with selection of suitable precursor, mixture of ethyl benzene and toluene may be selectively converted to para ethyl toluene; likewise para ethyl toluene is formed from dodecane or 1-butene, in addition to para-xylene; ethyl benzene may be selectively converted to diethyl benzene, propyl benzene may be converted to dipropyl benzene, and butyl benzene may be selectively converted to dibutylbenzene.

The following examples will serve to illustrate the process of the invention without limiting the same:

EXAMPLE 1

42.2 pounds of Q-Brand sodium silicate were mixed with 52.8 pounds of water. The resulting solution was designated Solution A. 1.35 pounds of commercial grade aluminum sulfate ($Al_2(SO_4)_3.14\ H_2O$)), 15.84 pounds of commercial grade NaCl, and 3.52 pounds of $H_2SO_4$ (96.06 wt. % $H_2SO_4$) were mixed with 72.2 pounds of water. The resulting solution was designated Solution B. Solution A and Solution B were mixed simultaneously in a nozzle and sprayed into an autoclave equipped with a paddle agitator. 2.84 pounds of tri-n-propylamine and 2.44 pounds of n-propyl bromide were added to the contents of the autoclave. The mixture was reacted at 316° F with 121 rpm agitation. After 14.1 hours at 316° F., the solid product was analyzed by X-ray diffraction and found to be 100% ZSM-5, having a $SiO_2/Al_2O_3$ ratio of 70.

A 10 gram sample of the above ZSM-5 was contacted with 500 ml. of 1 N $NH_4Cl$ solution. Three ion exchange steps were carried out, the first at 100° C. for 2 hours, the second at room temperature for 18 hours and the third at 100° C. for 3 hours. The exchanged product was thereafter calcined 1° C./minute to a temperature of 1000° F. and held at such temperature for 10 hours. The resulting HZSM-5 had a crystallite size of 1-2 microns. It was further characterized by a paraxylene sorption capacity of 6 weight percent and an ortho xylene sorption time for 30 percent of said capacity of 116 minutes. Both of the latter measurements were made at 120° C. For the para-xylene sorption the hydrocarbon partial pressure was 5.1 mm of mercury. For ortho xylene sorption time the hydrocarbon partial pressure was 3.8 mm of mercury.

EXAMPLE 2

Toluene was passed over the large crystal HZSM-5 catalyst of Example 1 at 1 atmosphere pressure and at temperatures between about 400° and about 650° C. at a weight hourly space velocity between 5 and 100. The reaction conditions and results, expressed in weight percent, are set forth in Table I below:

TABLE I

| Run | Time(hr) | Temp. °C | WHSV | Benzene | Toluene | Xylenes* p- | m- | o- | Total | $C_9^+$ | Conversion |
|---|---|---|---|---|---|---|---|---|---|---|---|
| 1 | 1.28 | 524 | 20 | 8.36 | 80.48 | 3.48 (31.29) | 5.46 (49.10) | 2.18 (19.60) | 11.12 | 0 | 19.5 |
| 2 | 2.18 | 521 | 50 | 2.78 | 93.00 | 1.76 (34.76) | 1.84 (43.81) | 0.60 (14.29) | 4.20 | 0 | 7.0 |
| 3 | 3.85 | 523 | 10 | 10.05 | 76.69 | 3.84 (29.18) | 6.72 (51.06) | 2.60 (19.76) | 13.16 | 0 | 23.3 |
| 4 | 4.27 | 503 | 100 | 1.38 | 95.98 | 1.08 (40.91) | 1.13 (42.80) | 0.43 (16.29) | 2.64 | 0 | 4.0 |
| 5 | 5.07 | 524 | 5 | 13.89 | 69.43 | 4.48 (26.94) | 8.61 (51.80) | 3.53 (21.26) | 16.61 | 0 | 30.6 |
| 6 | 5.40 | 525 | 20 | 6.87 | 83.97 | 2.97 (32.47) | 4.55 (49.67) | 1.63 (17.85) | 9.15 | 0 | 16.0 |
| 7 | 5.87 | 599 | 20 | 16.56 | 64.81 | 5.50 (29.63) | 9.45 (50.88) | 3.62 (19.51) | 18.58 | 0 | 35.2 |
| 8 | 6.18 | 598 | 50 | 9.16 | 79.26 | 4.69 (40.56) | 5.19 (44.84) | 1.69 (14.60) | 11.57 | 0 | 20.7 |
| 9 | 6.42 | 602 | 100 | 9.00 | 79.21 | 4.39 (37.25) | 5.42 (45.95) | 1.98 (16.79) | 11.79 | 0 | 20.8 |
| 10 | 7.83 | ~400 | 5 | 0.62 | 97.41 | 0.50 (26.28) | 1.00 (52.49) | 0.41 (21.24) | 1.91 | 0 | 2.6 |
| 11 | 23.02 | 398 | 5 | 0.59 | 97.48 | 0.48 (24.68) | 0.98 (50.65) | 0.48 (24.68) | 1.92 | 0 | 2.5 |
| 12 | 23.92 | 401 | 10 | 0.35 | 98.17 | 0.41 (27.62) | 0.81 (54.63) | 0.26 (17.76) | 1.48 | 0 | 1.8 |
| 13 | 24.70 | 524 | 20 | 3.97 | 90.38 | 2.03 (35.98) | 2.64 (46.77) | 0.98 (17.25) | 5.65 | 0 | 9.6 |
| 14 | 25.50 | 651 | 20 | 18.15 | 64.18 | 5.13 (29.05) | 8.93 (50.54) | 3.61 (20.41) | 17.7 | 0 | 35.8 |
| 15 | 25.72 | 650 | 50 | 7.04 | 84.17 | 3.32 (39.33) | 3.70 (43.87) | 1.42 (16.81) | 8.4 | 0 | 15.8 |
| 16 | 25.87 | 648 | 100 | 4.56 | 89.26 | 2.28 (36.86) | 2.81 (45.37) | 1.10 (17.77) | 6.18 | 0 | 10.8 |

*The values in parenthesis are the weight percent of xylene isomer in the total xylene fraction.

From the above results, it will be evident that paraxylene was selectively produced in an amount over the thermodynamic equilibrium concentration thereof in the total xylenes produced. It will further be seen that increasing the temperature within the range of 400° to 650° C. served to increase para-xylene selectivity substantially.

EXAMPLE 3

HZSM-5 having a crystallite size of about 0.03 micron was prepared as follows:

(a) Solution Preparation

| Silicate Solution | |
|---|---|
| 90.9 lb. | Q-Brand Sodium Silicate |
| 52.6 lb. | $H_2O$ |
| 118 g. | Daxad 27 (dispersant) |
| Acid Solution | |
| 1430 g. | $Al_2(SO_4)_3 \cdot xH_2O$ (M.W. = 595) |
| 3440 g. | $H_2SO_4$ |
| 4890 g. | NaCl |
| 54 lb. | $H_2O$ |
| Add'l Solids | |
| 2840 g. | NaCl |
| 2390 g. | n-propyl bromide |
| 4590 g. | MEK |
| Add'l Liquid | |
| 1180 g. | $H_2O$ |

(B) Procedure

The silicate solution and acid solution were mixed in a mixing nozzle to form a gel which was discharged into a 30 gallon autoclave to which 1180 grams of $H_2O$ had been previously added. The gel was whipped by agitation and 2840 grams of NaCl was added and thoroughly blended. The agitation was stopped and the organics solution was added as a layer on top of the gel. The autoclave was sealed and heated to about 220° F. without agitation and held there for 14–15 hours to prereact the organics. At the end of the prereaction period the agitation was commenced at 90 RPM to start the initial crystallization period. After about 75–80 hours the temperature was raised to 320 and held there for about three hours to complete crystallization. The excess or unreacted organics were flashed off and the contents of the autoclave were cooled and discharged. The product was analyzed by x-ray diffraction and shown to be 100% crystallinity ZSM-5 based upon a standard sample. Chemical analysis of the thoroughly washed crystalline product was:

| | % Wt. | Mole Ratio |
|---|---|---|
| $Al_2O_3$ | 2.21 | 1.0 |
| $SiO_2$ | 94.9 | 72.8 |
| Na | 0.81 | — |
| $Na_2O$ | — | 0.82 |
| N | 0.67 | 2.48 |
| C | 8.2 | 35.6 |

After thorough washing and drying at about 250° F. the zeolite was transformed into the catalytic form by the following steps:

(a) Precalcination in a 100% $N_2$ atmosphere for 3 hours at 1000° F., atmospheric pressure employing a programmed heat-up rate of 5° F./min to 1000° F. from ambient.

(b) Ion exchange with 1N $NH_4NO_3$ at room temperature for one hour using 5 cc of exchange solution per gram of dry zeolite.

(c) Washed with four volumes of water.

(d) Repeat steps (b) and (c) and dry at 250° F. in air.

The exchanged zeolite was analyzed and was found to contain 0.01 wt % Na. It was characterized by an ortho-xylene sorption capacity of 5.6 weight percent and an ortho xylene sorption time for 30 percent of said capacity of less than 1.3 minutes. Both of the latter measurements were made at 120° C. and a hydrocarbon partial pressure of about 3.8 mm. of mercury.

EXAMPLE 4

Toluene was passed over the microcrystalline HZSM-5 catalyst of Example 3 at 1 atmosphere pressure and at temperatures of 600°–650° C. at a weight hourly space velocity between 20 and 100. The reaction conditions and results expressed in weight percent are set forth in Table 2 below:

10 percent toluene conversion, use of the large crystals showed a 48 percent paraxylene selectivity as compared with 27 percent para-xylene selectivity with use of the small crystals.

EXAMPLE 5

A sample of the large crystal HZSM-5 catalyst of Example 1 was steamed for 2 hours at 560° C. in one atmosphere steam.

EXAMPLE 6

Toluene was passed over the large crystal HZSM-5 catalyst of Example 5 at 1 atmosphere pressure and at a temperature of approximately 650° C. at a weight hourly space velocity of 20. The reaction conditions and results are set forth in Table 3 below:

TABLE 3

| Time(hr) | Temp. °C | WHSV | Benzene | Toluene | Xylenes* p- | m- | o- | Total | $C_9+$ | Conversion |
|---|---|---|---|---|---|---|---|---|---|---|
| 0.58 | 650 | 20 | 8.82 | 81.83 | 4.36 (46.6) | 3.76 (40.2) | 1.22 (13.1) | 9.34 | 0.0 | 18.2 |
| 1.0 | 650 | 20 | 7.33 | 84.54 | 4.25 (52.3) | 2.98 (36.7) | 0.89 (11.0) | 8.13 | 0.0 | 15.5 |
| 1.72 | 650 | 20 | 6.62 | 86.43 | 3.94 (56.7) | 2.30 (33.2) | 0.71 (10.2) | 6.95 | 0.0 | 13.6 |
| 2.33 | 650 | 20 | 5.96 | 87.82 | 4.00 (64.3) | 1.72 (27.7) | 0.50 (8.0) | 6.22 | 0.0 | 12.2 |
| 3.0 | 650 | 20 | 5.31 | 88.90 | 4.24 (73.2) | 1.23 (21.3) | 0.32 (5.6) | 5.79 | 0.0 | 11.1 |
| 3.75 | 649 | 20 | 4.85 | 90.07 | 4.29 (84.4) | 0.61 (12.0) | 0.18 (3.6) | 5.08 | 0.0 | 9.9 |
| 5.0 | 649 | 20 | 3.38 | 93.08 | 3.47 (98.1) | 0.7 (1.9) | 0.0 (0.0) | 3.54 | 0.0 | 6.9 |
| 6.0 | 649 | 20 | 1.45 | 97.24 | 1.31 (100) | 0.0 (0.0) | 0.0 (0.0) | 1.31 | 0.0 | 2.8 |

*The values in parenthesis are the weight percent of xylene isomer in the total xylene fraction.

It will again be evident that with the use of large crystal HZSM-5 the amount of para-xylene produced was substantially greater than its equilibrium concentration, approaching 100 percent after 5–6 hours on stream.

TABLE 2

| Run No. | Time (hr) | Temp. °C | WHSV | Benzene | Toluene | Xylenes* p- | m- | o- | Total | $C_9+$ | Conversion |
|---|---|---|---|---|---|---|---|---|---|---|---|
| 1 | 1.0 | 600 | 50 | 7.26 | 84.85 | 1.97 (25.0) | 4.12 (52.2) | 1.80 (22.8) | 7.89 | 0.0 | 15.2 |
| 2 | 1.5 | 600 | 100 | 3.86 | 92.00 | 1.13 (27.2) | 2.12 (51.2) | 0.89 (21.5) | 4.15 | 0.0 | 8.0 |
| 3 | 2.28 | 650 | 100 | 5.18 | 89.61 | 1.55 (29.8) | 2.65 (51.0) | 1.00 (19.2) | 5.20 | 0.0 | 10.4 |

*The values in parenthesis are the weight percent of xylene isomer in the total xylene fraction.

From the above results, it will be seen that the amount of para-xylene in the total xylenes produced was essentially the thermodynamic equilibrium concentration.

FIG. 1 of the drawing shows a comparison of the para-xylene selectivity of the small, i.e. about 0.03 micron and large, i.e. about 1 micron crystal HZSM-5. It will be seen that para-xylene selectivity was greatly improved by use of the large crystal material. Thus, at

EXAMPLE 7

Toluene was co-fed along with hydrogen at a molar ratio of hydrogen to hydrocarbon of 2, over the large crystal HZSM-5 catalyst of Example 5 at 1 atmosphere pressure and at a temperature of approximately 650° C. at a weight hourly space velocity of 10. The reaction conditions and results are set forth in Table 4 below:

TABLE 4

| Time(hr) | Temp. °C | WHSV | Benzene | Toluene | Xylenes* p- | m- | o- | Total | $C_9+$ | Conversion |
|---|---|---|---|---|---|---|---|---|---|---|
| 0.25 | 649 | 10 | 6.32 | 84.82 | 4.26 (48.2) | 3.51 (39.7) | 1.08 (12.2) | 8.85 | 0.0 | 15.2 |
| 1.00 | 650 | 10 | 6.78 | 85.34 | 3.93 (49.9) | 3.04 (38.5) | 0.92 (11.6) | 7.88 | 0.0 | 14.7 |
| 2.00 | 650 | 10 | 6.75 | 85.35 | (3.94) (49.9) | 3.02 (38.3) | 0.93 (11.8) | 7.89 | 0.0 | 14.6 |
| 4.08 | 650 | 10 | 6.80 | 85.86 | 3.69 (50.2) | 2.82 (38.4) | 0.83 (11.4) | 7.34 | 0.0 | 14.1 |
| 6.00 | 650 | 10 | 6.49 | 85.97 | 3.90 (51.7) | 2.78 (36.8) | 0.87 (11.5) | 7.54 | 0.0 | 14.0 |
| 8.00 | 650 | 10 | 6.10 | 86.41 | 3.97 | 2.67 | 0.84 | 7.48 | 0.0 | 13.6 |

TABLE 4-continued

| Time(hr) | Temp. °C | WHSV | Benz-ene | Tolu-ene | Xylenes* | | | Total | C₉+ | Conver-sion |
|---|---|---|---|---|---|---|---|---|---|---|
| | | | | | p- | m- | o- | | | |
| | | | | | (53.1) | (35.7) | (11.2) | | | |

*The values in parenthesis are the weight percent of xylene isomer in the total xylene fraction.

Comparing the results of Tables 3 and 4, it will be seen that the presence of hydrogen, even at one atmosphere total pressure, greatly reduces the catalyst aging rate and thus significantly enhances the effective life of the catalyst while reducing the need for frequent regeneration.

EXAMPLE 8

Toluene was passed over a sample of the large crystal HZSM-5 catalyst of Example 5 at about 625° C. at a weight hourly space velocity (WHSV) of 20 and a pressure of 375 psig in the presence of hydrogen, the molar ratio of hydrogen to hydrocarbon being 6.

Initial conversion was 24.8 weight percent with a para-xylene selectivity (as percent of xylenes) of 45 percent. After a period of 14 days, conversion and para-xylene selectivity were 21 percent and 82 percent respectively.

Figure 2:
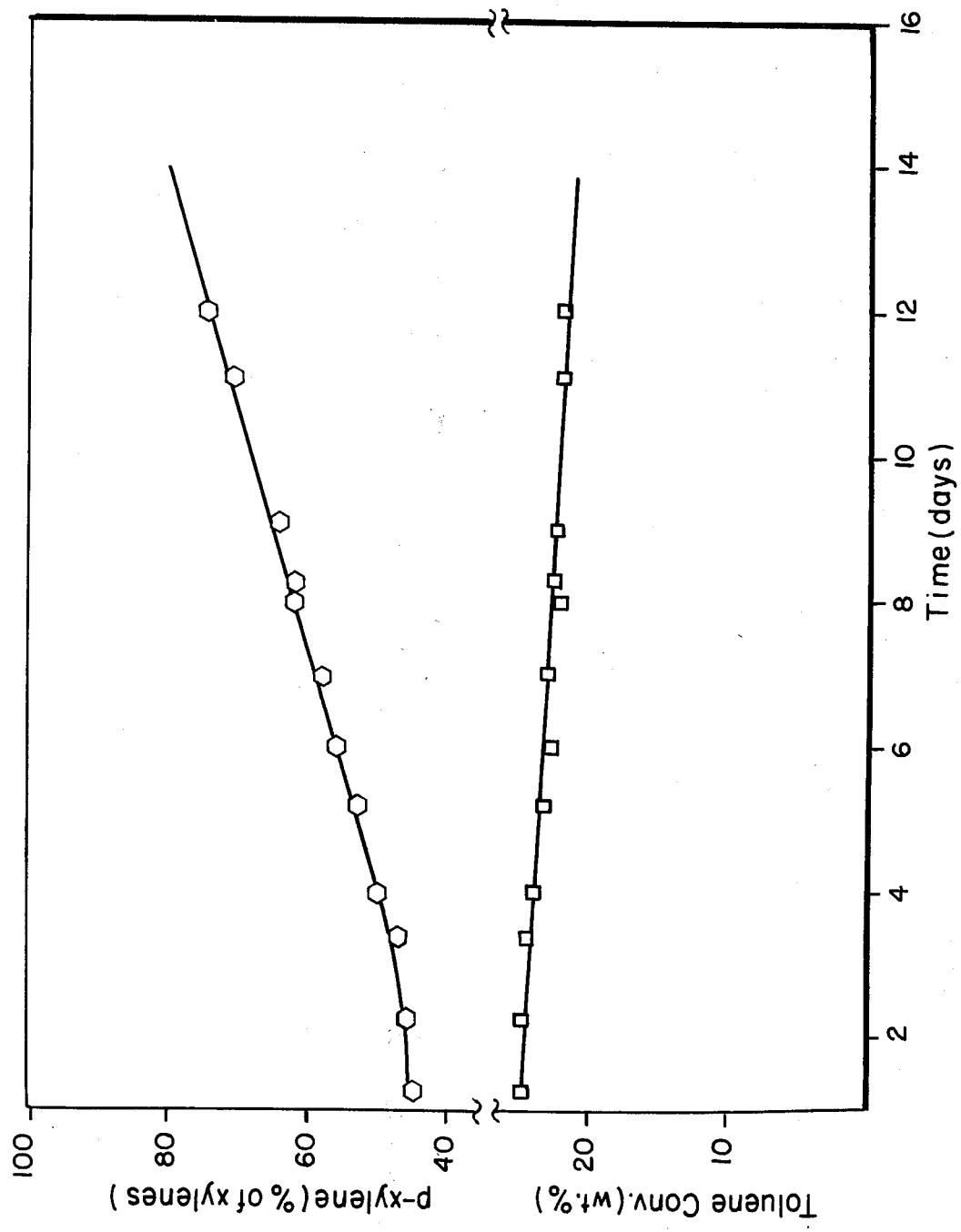
FIG. 2 shows the changes in toluene conversion and para-xylene selectivity occurring with time on stream utilizing a co-feed of toluene and hydrogen.

The changes in toluene conversion and para-xylene selectivity occurring during the course of the 14 day run are shown in FIG. 2. Referring more particularly to this Figure, it will be seen that the aging rate was modest, amounting to a 1.2 percent relative conversion loss per day. It will also be seen that during this period, para-xylene selectivity (as percent of xylenes) increased 2.9 percent per day.

EXAMPLE 9

A catalyst was prepared by heating 8.5 grams of ZSM-5 consisting of about 10 percent twinned crystals having up to 3 microns minimum dimension and about 90 percent of 5 to 10 microns polycrystalline spheroids for 5 hours at 1000° F. in air followed by three ion exchanges, at room temperature, with 500 ml. of 1 N NH₄Cl solution for 15.3 hours, 3.8 hours and 3.0 hours respectively. This material was then air calcined for 10 hours at 1000° F. The resulting product was characterized by a para-xylene sorption capacity of 6.2 weight percent and an ortho-xylene sorption time for 30 percent of said capacity of 43 minutes. Both of the latter measurements were made at 120° C. For the para-xylene sorption the hydrocarbon partial pressure was 5.1 mm. of mercury. For ortho xylene sorption time the hydrocarbon partial pressure was 3.8 mm. of mercury.

EXAMPLE 10

Toluene was passed over the catalyst of Example 9 at 600° C. at a weight hourly space velocity of 50 and one atmosphere pressure. Toluene conversion was 10.6 weight percent. The product consisted of 5.1 weight percent benzene, 89.4 weight percent toluene and 5.5 weight percent xylenes. The xylene fraction contained 35.2 percent para-xylene.

EXAMPLE 11

42.2 pounds of Q-Brand sodium silicate were mixed with 52.8 pounds of water. The resulting solution is designated Solution A. 1.35 pounds of commercial grade aluminum sulfate (Al₂(SO₄)3 . 14H₂O), 15.84 pounds of commercial grade NaCl, and 3.52 pounds of H₂SO₄(96.5 wt % H₂SO₄) were mixed with 72.2 pounds of water. The resulting solution is designated Solution B. 2.6 pounds of water were added to an autoclave equipped with high shear agitation. Solution A and Solution B were mixed simultaneously in a nozzle and sprayed into the autoclave. The resulting gel was mixed in the autoclave at 90 RPM and ambient temperature for one hour. 2.84 pounds of tri-n-propylamine and 2.44 pounds of n-propyl bromide were added to the contents of the autoclave. The mixture was reacted at 320° F. with 90 RPM agitation. After 20 hours at 320° F., the autoclave contents were sampled and the solid product was found to be 100% ZSM-5 by x-ray diffraction. After a total reaction time of 28.7 hours at 320° F., the autoclave contents were cooled. The resulting solid product was washed by decantation with deionized water and 3500 ppm Primafloc C-7 (Rohm & Haas) until the decant water was Cl⁻ free. The solid product was filtered and dried at 250° F.

500 grams of the dried filter cake product were calcined in N₂ for three hours at 1000° F.

444 grams of the calcined product were mixed with 2220 cc of 1 N NH₄NO₃ solution for 1 hour at ambient temperature. The mixture was vacuum filtered. The ion exchange procedure was repeated. The filter cake was washed with 1776 cc of water and the solid product was dried at 250° F. The sodium content of the final product was less than 0.01%.

The resulting catalyst had a crystal size of 1-2 microns, a para-xylene sorption capacity of 6.5 weight percent and an ortho-xylene sorption time for 30 percent of said capacity of 92 minutes. Both of the latter measurements were made at 120° C. For the para-xylene sorption the hydrocarbon partial pressure was 5.1 mm of mercury. For ortho xylene sorption time the hydrocarbon partial pressure was 3.8 mm of mercury.

EXAMPLE 12

The catalyst of Example 11 was contacted with 1-butene at 400° C. at a weight hourly space velocity of 4 and 1 atmosphere pressure. The liquid product which was 89 percent of the weight of charge contained 13.4 weight percent xylene and 3.9 weight percent ethyl toluene. The xylene fraction contained 37 percent p-xylene and the ethyl toluene fraction was 43 percent para ethyl toluene. Equilibrium values of these para isomers are 24 and 32 percent respectively.

EXAMPLE 13

The catalyst of Example 11 was contacted with dodecane at 400° C. at a weight hourly space velocity of 10 and 1 atmosphere pressure. The liquid product which was 41 weight percent of the charge consisted of 12.6 weight percent xylene and 4.3 weight percent ethyl toluene. The xylene fraction was 63 percent para-xylene and the ethyl toluene fraction was 58 percent para-ethyltoluene.

EXAMPLE 14

The catalyst of Example 11 was contacted with toluene at 500° C., at a weight hourly space velocity of 50, a pressure of 375 psig and a hydrogen to hydrocarbon molar ratio of 6. The liquid product which contained 20 weight percent of converted toluene consisted of 12.1 weight percent xylenes in addition to benzene, with the xylene fraction containing 30 percent of paraxylene.

EXAMPLE 15

The catalyst of Example 11 was treated with toluene for 5 hours at 640° C. at a weight hourly space velocity of 50 and one atmosphere pressure to deposit about 4 weight percent coke thereon. The treated catalyst sorbed 6.1 grams of para-xylene per 100 grams of zeolite at 120° C. and a para-xylene pressure of 5.1 mm. of mercury. At 120° C. and on ortho-xylene pressure of 3.8 mm. of mercury, the time for sorption of 30 percent of xylene capacity was 6000 minutes. The catalyst had an alpha value of 281. The catalyst, containing approximately 4 weight percent of coke, was contacted with toluene at 550° C., a pressure of 600 psig, a weight hourly space velocity of 40 and a hydrogen to hydrocarbon mole ratio of 10. The liquid product contained 80.7 weight percent toluene (19.3 percent conversion) and 9.6 weight percent xylenes in addition to benzene. The xylene fraction contained 82 percent of para-xylene.

EXAMPLE 16

Three grams of the catalyst of Example 11 were contacted with a solution consisting of 1.02 grams of magnesium acetate tetrahydrate in 4 cc of water. The resulting slurry was evaporated to dryness over a 24 hour period and then air calcined for 10 hours at 1000° F. to yield a product of HZSM-5 containing 6 weight percent of MgO.

EXAMPLE 17

The catalyst of Example 16 was contacted with toluene at 550° C., a pressure of 600 psig, a weight hourly space velocity of 40 and a hydrogen to hydrocarbon ratio of 4. Toluene conversion was 29.4 percent. The liquid product contained 15.03 weight percent xylene, which consisted of 53 percent of the para isomer.

EXAMPLE 18

This example illustrates the production of p-diethylbenzene with catalyst of Example 11 pretreated with toluene as in Example 15 to deposit approximately 4 weight percent of coke. A mixture of benzene and ethylene at a mole ratio of 1:2 (fresh feed) is mixed with a recycle stream containing benzene and ethylbenzene and passed over the catalyst at a temperature of 825°-850° F., a pressure of 300 psig and a WHSV of 2, based on lb. ethylene per hour per lb. catalyst. The reactor effluent is distilled to yield an overhead fraction (recycle stream) consisting of benzene, ethylbenzene and unreacted ethylene which is recycled to the reactor and a bottom fraction containing the desired product, p-diethylbenzene.

EXAMPLE 19

Toluene was passed over the microcrystalline HZSM-5 catalyst of Example 3 at 1 atmosphere pressure, 1112° F., and a weight hourly space velocity of 50. The toluene conversion was 15 weight percent and the p-xylene yield, as percent of xylenes, was 25 percent, i.e., approximately the normal equilibrium concentration of p-xylene.

EXAMPLE 20

Catalyst prepared as in Example 3 was combined with alumina to produce an extruded catalyst consisting of 65 weight percent zeolite and 35 weight percent alumina. Following use for toluene disproportionation under a variety of conditions and regeneration, toluene was passed over this catalyst at 885°-970° F., WHSV = 5-6.3, pressure = 450 psig and a hydrogen to hydrocarbon ratio of 0.5 for 38 days.

The coke level was 45 grams per 100 grams of catalyst. The p-xylene sorption capacity, measured at a p-xylene pressure of 5.1 mm of mercury, was 2 grams per 100 grams of zeolite and the o-xylene sorption time for 30% of xylene sorption capacity was 2900 minutes; this measurement was at an o-xylene pressure of 3.8 mm of mercury. The catalyst had an alpha value of 20. Toluene was passed over the catalyst at 970° F., 450 psig, WHSV = 6.3 and a hydrogen to hydrocarbon ratio of 0.5. The toluene conversion was 37 weight percent and the p-xylene yield, as percent of xylenes produced, was 43.

EXAMPLE 21

A catalyst was prepared by adding 3 grams of the catalyst of Example 1 to a solution made from 0.3 grams of magnesium nitrate hexahydrate 2.2 ml of water. The slurry was mixed thoroughly and air calcined by heating 3° F. per minute to 1000° F. followed by 10 hours at 1000° F. The resultant catalyst contained 2.4 weight percent magnesium. It sorbed 5.2 grams of p-xylene per 100 grams of zeolite at 120° C. and a p-xylene pressure of 5.1 mm of mercury. At 120° C. and a o-xylene pressure of 3.8 mm of mercury, the time for sorption of 30 percent of xylene capacity was 2600 minutes. The catalyst had an alpha value of 36.

EXAMPLE 22

Toluene was passed over the catalyst of Example 21 at 1022° F., 600 psig, hydrogen to hydrocarbon ratio of 4 and a WHSV of 10. The toluene conversion was 20 weight percent and the p-xylene yield, as percent of xylenes, was 45.

EXAMPLE 23

A five gram sample of the HZSM-5 catalyst of the type described in Example 3 was placed in a glass tube fitted with a fritted glass disc. Dimethylsilane was passed through the bed of HZSM-5 at a rate of 40 cc/minute. After 15 minutes, the HZSM-5 had sorbed 0.60 gram of dimethylsilane. The product was added to 200 cc of 15 percent aqueous ammonia to hydrolyze the silane. Hydrogen was evolved rapidly. After one hour, the product was filtered and calcined at 1° C./minute to 538° C. and held at this temperature for 6 hours.

The above procedure was repeated a total of three times to yield a silica-loaded HZSM-5 containing 5 weight percent of added silica.

This catalyst sorbed 4.1 grams of o-xylene per 100 grams of zeolite at 120° C. and an o-xylene pressure of 3.8 mm of mercury. The sorption reached 30 percent of capacity in 2.7 minutes. The catalyst had an alpha value of 75.

EXAMPLE 24

Toluene was passed over the catalyst of Example 23 at 1112° F., one atmosphere pressure, WHSV = 40 and a hydrogen to hydrocarbon ratio of 2. The toluene conversion was 2 weight percent and the p-xylene yield, as percent of xylenes, was 62. At more realistic toluene conversion, e.g. 20 percent, the selectivity to para-xylene was only 27 percent, i.e. substantially the same as equilibrium, indicating that the sorption time to reach 30 percent of capacity of only 2.7 minutes was too low.

EXAMPLE 25

Twenty grams of NH$_4$-ZSM-5 of 0.03 micron crystal size was suspended in a solution of 5.35 grams of ortho boric acid in 40 ml of water at a temperature of 80° C. After standing overnight (16.5 hours) at 90° C. the contents were poured into a 30 × 50 mm crystallizing dish and placed in an oven at 110° C. The contents were stirred frequently until a uniform dry powder was formed. The temperature was gradually increased to 200° C. and the catalyst allowed to stand for 1–2 hours. It was then transferred to a furnace at 500° C., in air, in the same open crystallizing dish for a period of 17.5 hours. The theoretical amount of boron, present as the oxide, was 4.06 wt % B. The powder was pressed into wafers, crushed and screened to 14–20 mesh size for use.

This catalyst sorbed 3.1 grams of p-xylene at 120° C. and a p-xylene pressure of 5.1 mm of mercury. At 120° C. and an o-xylene pressure of 3.8 mm of mercury, the time for sorbing 30 percent of capacity was 270 minutes. The catalyst had an alpha value of 3.8.

EXAMPLE 26

Toluene was passed over 5 grams of the catalyst of Example 25 at 1112° F., one atmosphere pressure, and a WHSV = 4.5. The toluene conversion was 11.9 weight percent and the p-xylene yield, as percent of the xylenes, was 74.

EXAMPLE 27

Ten (10.0) grams of zeolite of the type described in Example 3 was mixed with 6.5 grams of antimony trimethoxide and 75 cc of p-xylene. This slurry was refluxed over nitrogen gas for 17 hours. The solids were then washed with 100 cc of toluene, then 100 cc of methanol followed by 100 cc of n-hexene. The product was air dried then placed in a vacuum oven at 100° C. for 3 hours. It was then air calcined for 10 hours at 1000° F. The product contained 24 weight percent antimony.

The catalyst sorbed 3.5 grams of p-xylene per 100 grams of zeolite at 120° C. and a p-xylene pressure of 5.1 mm of mercury. At 120° C. and a o-xylene pressure of 3.8 mm of mercury, the time for sorption of 30 percent of xylene capacity was 89 minutes. The catalyst had an alpha value of 8.

EXAMPLE 28

10 grams of the ammonium form of ZSM-5 was suspended in a solution of 5 grams of uranium dioxide dinitrate hexahydrate in 20 cc of water. The slurry was heated to a temperature of 73° C. and allowed to stand overnight. The entire contents of the flask were then poured into a crystallizing dish and placed in an oven at 130° C. The catalyst was stirred every 30 minutes. After about 2 hours, the catalyst had a dry appearance. It was then placed in an oven at 500° C. and allowed to stand overnight. The final weight of the calcined catalyst was 12.17 grams. The catalyst had a xylene sorption capacity at 120° C. and a xylene pressure of 4.5 ± 0.8 mm. mercury of 6.3 grams xylene per 100 grams of zeolite. The time to sorb ortho-xylene at 120° C. and 3.8 mm. pressure to an extent of 30 percent of the capacity was 4.8 minutes. The catalyst had an alpha value of 83.

EXAMPLE 29

Toluene was passed over the catalyst of Example 28 at 1022° F., one atmosphere pressure, and a WHSV of 3.5. The toluene conversion was 46 weight percent and the p-xylene yield, as percent of xylenes, was 24.

EXAMPLE 30

11.6 grams of magnesium acetate tetrahydrate were dissolved in 25 ml of water. To this was added 10 grams of ⅛ pellets of the ammonium form of ZSM-5 zeolite crystal. After soaking for a few minutes, the excess liquid was withdrawn and held. The catalyst was placed in an oven to drive off the water. After cooling, the dry catalyst was placed in the remaining solution of magnesium acetate. Excess liquid was withdrawn and the wet catalyst placed in an oven to dry. This procedure was repeated until all of the liquid had been absorbed by the catalyst. Finally, the catalyst was placed in a furnace at 500° C. overnight. The weight of the final catalyst was 11.56 grams. The catalyst had a xylene sorption capacity of 120° C. and a xylene pressure of 4.5 ± 0.8 mm mercury of 4.2 grams xylene per 100 grams of zeolite. The time to sorb ortho-xylene at 120° C. and 3.8 mm pressure to an extent of 30 percent of the capacity was 7.5 minutes. The catalyst had an alpha value of 21.

EXAMPLE 31

Toluene was passed over the catalyst of Example 30 at 1022° F., one atmosphere pressure, and a WHSV of 3.5. Toluene conversion was 12 weight percent and the p-xylene yield, as percent of xylenes, was 25.

EXAMPLE 32

10 grams of ammonium ZSM-5 were added to a solution of 7.28 grams of zinc nitrate hexahydrate in 20 ml of water. Suspension was heated to approximately 90° C. and allowed to stand overnight. The entire contents of the flask were then poured into a crystallizing dish and placed in an oven at about 130° C. After about 2 hours, the catalyst was placed in a furnace at 500° C. and allowed to stand for about 8 hours. Final weight of the catalyst after calcination was 11.21 grams. The catalyst had a xylene sorption capacity of 120° C. and a xylene pressure of 4.5 ± 0.8 mm memory of 4.9 grams of xylene per 100 grams of zeolite. The time to sorb ortho-xylene at 120° C. and 3.8 mm pressure to an extent of 30 percent of the capacity was 38 minutes. The catalyst had an alpha value of 504.

EXAMPLE 33

Toluene was passed over the catalyst of Example 32 at 1022° F., one atmosphere, and a WHSV of 3.5. The toluene conversion was 20 weight percent and the p-xylene yield, as percent of xylenes, was 28.

EXAMPLE 34

10 grams of the acid form of ZSM-5 were suspended in a solution of 12.9 grams of calcium nitrate tetrahydrate in 25 ml of water. The slurry was heated to 88° C. and allowed to stand overnight. The entire contents were then poured into a crystallizing dish and placed in an oven at 100°–130° C. After about 4 hours the temperature was raised to 200° C. for approximately 2 hours. The catalyst was then placed in a furnace at 500° C.

overnight. Final weight of the catalyst after calcination is 12.80 grams. The catalyst had a xylene sorption capacity at 120° C. and a xylene pressure of 4.5 ± 0.8 mm mercury of 1.2 grams of xylene per 100 grams of zeolite. The time to absorb ortho-xylene at 120° C. and 3.8 mm pressure to an extent of 30 percent of the capacity was 116 minutes. The catalyst had an alpha value of 0.9.

EXAMPLE 35

Toluene was passed over the catalyst of Example 34 at 1022° F., one atmosphere pressure, and a WHSV of 3.5. Toluene conversion was 0.4 weight percent and the p-xylene yield, as percent of xylenes, was 67.

EXAMPLE 36

10 grams of the ammonium form of powdered ZSM-5 were placed in a solution of 11.6 grams of magnesium acetate tetrahydrate in 25 ml of water. The suspension was heated to a temperature of 95° C. and allowed to stand overnight. The entire contents of the flask were then poured into a crystallizing dish and placed in an oven at 56° C. The temperature was then turned up to 100°-120° C. The slurry was stirred frequently until the catalyst developed a dry appearance. Temperature was then gradually raised to 200° C. and held for about 1 hour. The catalyst was then placed in a furnace at 500° C. overnight. The final weight of the catalyst was 11.37 grams. The catalyst had a xylene sorption capacity at 120° C. and a xylene pressure of 4.5 ± 0.8 mm mercury of 4.4 grams of xylene per 100 grams of zeolite. The time to sorb ortho-xylene at 120° C. and 3.8 mm pressure to an extent of 30 percent of the capacity was 655 minutes. The catalyst had an alpha value of 24.

EXAMPLE 37

Toluene was passed over the catalyst of Example 36 at 1022° F., one atmosphere pressure, and a WHSV of 4.5. The toluene conversion was 16 weight percent and the p-xylene yield, as percent of xylenes, was 59.

EXAMPLE 38

A boron-containing ZSM-5 catalyst was prepared according to the procedure of Example 25; except that 0.22 grams of ortho boric acid was used per gram of ammonium-ZSM-5. The finished catalyst is calculated to contain 3.34 weight % B, probably present as the oxide.

Propylene was passed over the above catalyst at WHSV = 2.6 at 400° C. The conversion was 94%. The aromatics produced (25 wt.%) contained 31% xylenes. The p-xylene content of the xylene fraction was 56%.

EXAMPLE 39

A sample of HZSM-5 was mixed with reagent $Sb_2O_3$ in a ratio of 0.43 g $Sb_2O_3$ per gram of HZSM-5. After pressing and screening to 8/14 mesh, about one gram was charged to a micro glass reactor of 15–20 cm length × 14–18 mm diameter. A 4–6 mm thermowell was located in the catalyst bed. The catalyst was heated to 525° C. during one hour in 50 cc/min flowing nitrogen, holding in nitrogen for three hours at 500°-525°, followed by air (50 cc/min) for 0.5 hours. The resultant catalyst contained 30% $Sb_2O_3$.

EXAMPLE 40

A sample of 30% $Sb_2O_3$/HZSM-5, prepared according to Example 39 was placed in a vertical flow reactor; propylene was passed over the catalyst at 400° C. at WHSV = 3.0. Propylene conversion was 90.3%. Aromatics were produced in 14.8% selectivity, containing benzene, toluene, xylenes and ethyltoluene as a major components. The largest fraction (34%) was xylene which contained 91% of the para isomer.

EXAMPLE 41

Another sample of 30% $Sb_2O_3$/HZSM-5 of Example 39 was used for selective toluene disproportionation. Toluene was passed over the catalyst in a vertical fixed-bed flow reactor at 550° C. and atmospheric pressure at a WHSV = 1.0. After 6 hours on stream, the conversion of toluene was 20%. Products were benzene and xylenes. The xylenes contained 81% of the para isomer.

EXAMPLE 42

Another sample of $Sb_2O_3$-ZSM-5 was prepared following the procedure of Example 39 except that 0.33 g $Sb_2O_3$ was used per gram of HZSM-5. The resultant catalyst contained nominally 25% $Sb_2O_3$.

EXAMPLE 43

The catalyst prepared in Example 42 was used in toluene disproportionation to benzene and xylene at atmospheric pressure, 550° F. and 1 WHSV. After 6 hours on stream, toluene conversion was 9.5%. The xylene fraction contained 83% p-xylene.

The catalyst sorbed 1.39 grams of p-xylene per 100 grams of zeolite at 120° C. and a p-xylene pressure of 5.1 mm Hg. At 120° C. and an o-xylene pressure of 3.8 mm Hg, the time for sorption of 30% of xylene capacity, 0.3, exceeded 300 minutes.

EXAMPLE 44

This example illustrates the production of p-diethyl-benzenes with catalyst of Example 11 pretreated with toluene as in Example 15 to deposit approximately 4 weight percent of coke. A mixture of benzene and ethylene at a mole ratio of 1:2 (fresh feed) is mixed with a recycle stream containing benzene and ethylbenzene and passed over the catalyst at a temperature of 825°-850° F., a pressure of 300 psig and a WHSV of 2, based on lb. ethylene per hour per lb. catalyst. The reactor effluent is distilled to yield an overhead fraction (recycle stream) consisting of benzene, ethylbenzene and unreacted ethylene which is recycled to the reactor and a bottom fraction containing the desired product, p-diethylbenzene.

EXAMPLE 45

The feed in this example was a hydrogenated octene-decene oligomer consisting of paraffins of about the following composition: <0.5% dimer ($C_{16}$–$C_{20}$), 40% trimer ($C_{24}$–$C_{30}$), 35% tetramer ($C_{34}$–$C_{40}$), 20% pentamer ($C_{44}$–$C_{50}$) and 5% hexamer (up to $C_{60}$).

The feed was passed downward through a vertical fixed bed flow reactor containing large crystal HZSM-5 of 1–2μ minimum crystal dimension. At a temperature of 350° C., a weight hourly space velocity of 1.0 and atmospheric pressure, the conversion was 73%.

The product was a mixture of about 10% gaseous and 90% liquid light products that contained appreciable quantities of $C_6$ to $C_{10}$ aromatic hydrocarbons. The xylene fraction contained approximately 60% paraxylene, and 40% m- and o-xylene. Conventional catalysts produce much less aromatics with only about 24% paraxylene in xylenes.

A weight hourly space velocity of 2.0, the conversion was 50%. The product distribution was similar to that noted above obtained at WHSV of 1.0

The specific para-dialkylaromatic selectivity obtainable with the catalysts described herein depends on the particular feed and the operating conditions. In toluene disproportionation, the para-xylene content of the xylenes produced is highest at low toluene conversion. In addition, the catalysts of this invention have been found to exhibit a very surprising and unusual phenomenon, namely, at a given percent toluene conversion, the para-xylene selectivity is increased as the temperature is increased over the approximate range of 400° to 700° C.

For the purposes of comparing the para-selectivity of different catalysts, it is therefore desirable to compare them at the same operating temperature, e.g., 550° C. and the same percent toluene conversion, e.g., 20%, by adjusting the toluene feed rate. Para-selectivity may be obtained for these reference conditions directly or by extrapolation from other actual operating conditions.

Para-xylene selectivities (% p-xylene in total xylenes) for the above standard conditions (20% toluene conversion at 550° C.) and ortho-xylene sorption times, $t_o$.3 (30% of capacity at 120° C.) are shown in the following table:

TABLE 5

| Catalyst of Example | Ortho-Xylene Sorption time, $t_o$.3 (min) | Para-xylene Selectivity+ | Selectivity++ Fractor |
|---|---|---|---|
| 3 | <1.3 | 24 | 0 |
| 23 | 2.7 | 27 | 3.7 |
| 28 | 4.8 | 25 | 1.3 |
| 30 | 7.5 | 24 | 0 |
| 32 | 38 | 28 | 5.4 |
| 11 | 92 | 39 | 20 |
| 34 | 116 | 38 | 18 |
| 25 | 270 | 48 | 32 |
| 17 | 583 | 69 | 59 |
| 36 | 655 | 53 | 38 |
| 21 | 2600 | 45 | 28 |
| 20 | 2900 | 69 | 59 |
| 15 | 6000 | 80 | 73 |

+From toluene, 550° C, 20% toluene conversion. 24% p-xylene represents the equilibrium composition and hence no unusual selectivity.

Figure 3:
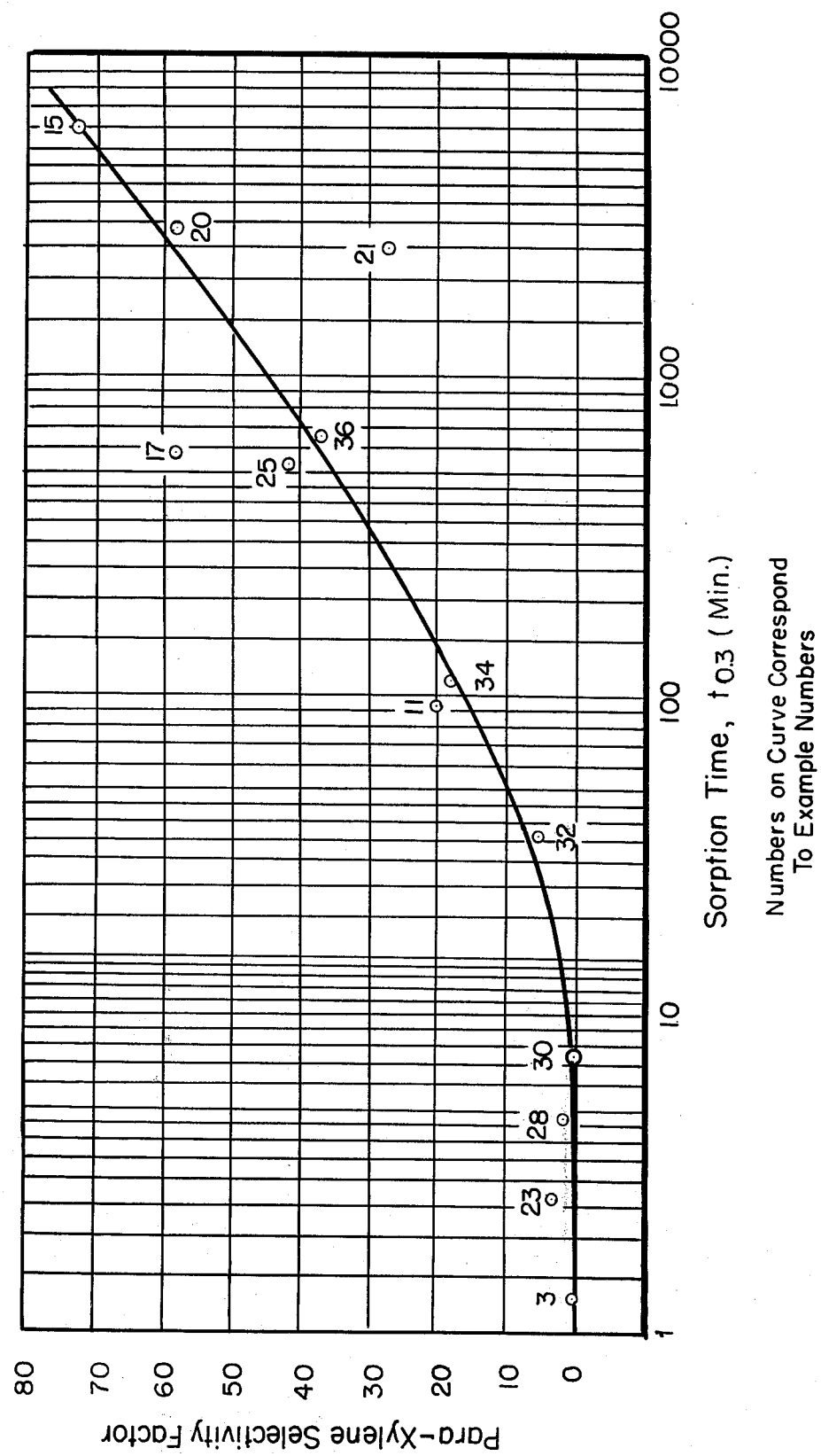
FIG. 3 shows change in para-xylene selectivity with variation of ortho-xylene sorption time for 30 percent of xylene sorption capacity of the zeolite catalyst used.

++Selectivity factor $= \left( \dfrac{\text{\% p-xylene in sylenes} - 24}{76} \right) 100$ The above data are presented graphically in the FIG. 3 where the para-xylene selectivity factor is plotted against the ortho-xylene sorption time for 30 percent of capacity. By reference to this Figure, it can be readily seen that catalysts having a xylene sorption time for 30 percent of xylene sorption capacity of greater than 10 minutes are para-xylene selective.

It is to be understood that the foregoing description is merely illustrative of preferred embodiments of the invention, of which many variations may be made by those skilled in the art within the scope of the following claims without departing from the spirit thereof.

We claim:

1. A process for the selective production of para dialkyl substituted benzenes wherein the alkyl group contains from 1 to 4 carbon atoms which comprises contacting, under conversion conditions, a hydrocarbon precursor selected from the group consisting of mono alkyl-substituted benzenes having 1–4 carbon atoms in the alkyl substituent, $C_2$-$C_{15}$ olefin and $C_3$-$C_{60}$ paraffin or mixtures thereof including mixtures of benzene with at least one of the aforementioned olefins or paraffins with a catalyst characterized by a xylene sorption capacity greater than 1 gram/100 grams of zeolite and an ortho xylene sorption time for 30 percent of said capacity of greater than 10 minutes, said sorption capacity and sorption time being measured at 120° C. and a xylene pressure of 4.5 ± 0.8 mm. of mercury, said catalyst comprising a crystalline aluminosilicate zeolite having a silica to alumina ratio of at least about 12 and a constraint index within the approximate range of 1 to 12 and separating a para dialkyl substituted benzene from the resulting product.

2. The process of claim 1 wherein said conversion conditions include a temperature between about 250° and about 750° C., a pressure between about 0.1 atmosphere and about 100 atmospheres utilizing a weight hourly space velocity of between 0.1 and about 2000.

3. The process of claim 1 wherein conversion takes place in the presence of hydrogen, with hydrogen/precursor mole ratio being between about 2 and about 20.

4. The process of claim 1 wherein said catalyst is characterized by an activity, in terms of alpha value, of between about 2 and about 5000.

5. The process of claim 1 wherein said crystalline aluminosilicate zeolite has a minimum crystal dimension greater than about 0.5 micron.

6. The process of claim 1 wherein toluene is disproportionated.

7. The process of claim 6 wherein conversion conditions include a temperature between about 400° and about 700° C. at a pressure between about 1 atmosphere and about 100 atmospheres utilizing a weight hourly space velocity of between about 1 and about 50.

8. The process of claim 1 wherein the para dialkyl substituted benzene is para-xylene.

9. The process of claim 1 wherein the para dialkyl substituted benzene is para ethyl toluene.

10. The process of claim 1 wherein the para dialkyl substituted benzene is para diethylbenzene.

11. The process of claim 1 wherein said precursor is a $C_2$-$C_{15}$ olefin.

12. The process of claim 11 wherein conversion conditions include a temperature between about 300 and about 700° C. at a pressure between about atmospheric and 100 atmospheres utilizing a weight hourly space velocity between about 1 and about 1000.

13. The process of claim 1 wherein said precursor is a $C_3$-$C_{60}$ paraffin.

14. The process of claim 13 wherein conversion conditions include a temperature between about 300° and about 700° C. at a pressure between atmospheric and about 100 atmospheres utilizing a weight hourly space velocity between about 0.1 and about 100.

15. The process of claim 1 wherein said crystalline aluminosilicate zeolite is ZSM-5.

16. The process of claim 1 wherein the minimum crystal dimension of said crystalline aluminosilicate zeolite is within the approximate range of 1 to 20 microns.

17. The process of claim 1 wherein the minimum crystal dimension of said crystalline aluminosilicate zeolite is within the approximate range of 1 to 6 microns.

18. The process of claim 15 wherein the ZSM-5 is predominantly in the hydrogen form.

19. The process of claim 15 wherein the ZSM-5 is present in combination with a binder therefor.

20. The process of claim 15 wherein the conversion takes place in the presence of hydrogen, with the hydrogen/precursor mole ratio being between about 2 and about 20.

21. The process of claim 1 wherein said zeolite has undergone modification prior to use in the selective production of para dialkyl substituted benzenes by combining between about 1 and about 40 weight percent coke therewith.

22. The process of claim 1 wherein said zeolite has undergone modification prior to use in the selective production of para alkyl substituted benzenes by combining between 2 and about 30 weight percent of a difficulty reducible oxide therewith.

23. The process of claim 21 wherein said difficulty reducible oxide is magnesium oxide.

24. The process of claim 21 wherein the crystalline aluminosilicate has a minimum crystal dimension greater than about 0.5 micron.

25. The process of claim 22 wherein the crystalline aluminosilicate has a minimum crystal dimension greater than about 0.5 micron.

* * * * *

UNITED STATES PATENT AND TRADEMARK OFFICE
CERTIFICATE OF CORRECTION

PATENT NO. : 4,117,026

DATED : September 26, 1978

INVENTOR(S) : Werner O. Haag and David H. Olson

It is certified that error appears in the above-identified patent and that said Letters Patent are hereby corrected as shown below:

Column 3, line 12, "t" should read --to--.

Column 8, line 16, "foudn" should read --found--.

Column 22, line 3, Delete the word "a".

Column 23, line 42, "sylenes" should read --xylenes--.

Signed and Sealed this

Twenty-fifth Day of September 1979

[SEAL]

Attest:

LUTRELLE F. PARKER

Attesting Officer    Acting Commissioner of Patents and Trademarks